(12) United States Patent
Esch et al.

(10) Patent No.: US 8,454,688 B2
(45) Date of Patent: *Jun. 4, 2013

(54) ACCOMMODATING INTRAOCULAR LENS HAVING PERIPHERALLY ACTUATED DEFLECTABLE SURFACE AND METHOD

(75) Inventors: Victor Esch, Albuquerque, NM (US);
John Scholl, San Ramon, CA (US);
Terry Smiley, San Francisco, CA (US);
Patrick Myall, San Francisco, CA (US);
Bill Evans, San Francisco, CA (US);
Barry Cheskin, Los Altos, CA (US);
Henry Wu, Belmont, CA (US)

(73) Assignee: PowerVision, Inc., Belmont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/853,892

(22) Filed: Aug. 10, 2010

(65) Prior Publication Data
US 2010/0324672 A1  Dec. 23, 2010

Related U.S. Application Data

(63) Continuation of application No. 11/715,221, filed on Mar. 6, 2007, now abandoned, which is a continuation of application No. 11/252,916, filed on Oct. 17, 2005, now Pat. No. 7,217,288, which is a continuation-in-part of application No. 10/971,598, filed on Oct. 22, 2004, now Pat. No. 7,261,737, which is a continuation-in-part of application No. 10/734,514, filed on Dec. 12, 2003, now Pat. No. 7,122,053.

(60) Provisional application No. 60/433,046, filed on Dec. 12, 2002.

(51) Int. Cl.
*A61F 2/16* (2006.01)

(52) U.S. Cl.
USPC .......................................... 623/6.13

(58) Field of Classification Search
USPC ................... 623/6.11, 6.13, 6.22, 6.34, 6.37
See application file for complete search history.

(56) References Cited

U.S. PATENT DOCUMENTS

| 4,111,995 A | 9/1978 | Nelson |
| 4,253,199 A | 3/1981 | Banko |
| 4,254,509 A | 3/1981 | Tennant |

(Continued)

FOREIGN PATENT DOCUMENTS

| EP | 0898972 A2 | 3/1999 |
| FR | 2784575 | 4/2000 |

(Continued)

OTHER PUBLICATIONS

Anvar et al.; U.S. Appl. No. 13/033,474 entitled "Fluid for Accommodating Intraocular Lenses," filed Feb. 23, 2011.

(Continued)

*Primary Examiner* — William H Matthews
(74) *Attorney, Agent, or Firm* — Shay Glenn LLP

(57) ABSTRACT

An accommodating intraocular lens is provided in which a deflectable lens element is anchored to a substrate along its optical axis to define a fluid filled space. Fluid-filled haptics disposed in fluid communication with the space vary the fluid volume in the space responsive to forces applied by the ciliary muscles, thereby causing the periphery of the lens element to deflect relative to the substrate and changing the optical power of the intraocular lens.

5 Claims, 7 Drawing Sheets

U.S. PATENT DOCUMENTS

| | | |
|---|---|---|
| 4,304,895 A | 12/1981 | Loshaek |
| 4,373,218 A | 2/1983 | Schachar |
| 4,409,691 A | 10/1983 | Levy |
| 4,423,809 A | 1/1984 | Mazzocco |
| 4,435,856 A | 3/1984 | L'Esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | McClure |
| 4,528,311 A | 7/1985 | Beard et al. |
| 4,575,373 A | 3/1986 | Johnson |
| 4,585,457 A | 4/1986 | Kalb |
| 4,604,295 A | 8/1986 | Humphreys |
| 4,615,701 A | 10/1986 | Woods |
| 4,620,954 A | 11/1986 | Singer et al. |
| 4,685,921 A | 8/1987 | Peyman |
| 4,685,922 A | 8/1987 | Peyman |
| 4,693,717 A | 9/1987 | Michelson |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,764,423 A | 8/1988 | Yamaguchi et al. |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turley |
| 4,902,293 A | 2/1990 | Feaster |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,145,884 A | 9/1992 | Yamamoto et al. |
| 5,145,935 A | 9/1992 | Hayashi |
| 5,152,789 A | 10/1992 | Willis |
| 5,171,266 A | 12/1992 | Wiley et al. |
| 5,200,430 A | 4/1993 | Federman |
| 5,201,763 A | 4/1993 | Brady et al. |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,326,347 A | 7/1994 | Cumming |
| 5,391,590 A | 2/1995 | Gerace et al. |
| 5,405,386 A | 4/1995 | Rheinish et al. |
| 5,443,506 A | 8/1995 | Garabet |
| 5,444,106 A | 8/1995 | Zhou et al. |
| 5,444,135 A | 8/1995 | Cheradame et al. |
| 5,476,514 A | 12/1995 | Cumming |
| 5,489,302 A | 2/1996 | Skottun |
| 5,496,366 A | 3/1996 | Cumming |
| 5,506,300 A | 4/1996 | Ward et al. |
| 5,512,609 A | 4/1996 | Yang |
| 5,578,081 A | 11/1996 | McDonald |
| 5,585,049 A | 12/1996 | Grisoni et al. |
| 5,593,436 A | 1/1997 | Langerman |
| 5,607,472 A | 3/1997 | Thompson |
| 5,628,795 A | 5/1997 | Langerman |
| 5,633,504 A | 5/1997 | Collins et al. |
| 5,665,822 A | 9/1997 | Bitler et al. |
| 5,674,282 A | 10/1997 | Cumming |
| 5,697,973 A | 12/1997 | Peyman et al. |
| 5,702,441 A | 12/1997 | Zhou |
| 5,774,273 A | 6/1998 | Bornhorst |
| 5,776,191 A | 7/1998 | Mazzocco |
| 5,776,192 A | 7/1998 | McDonald |
| 5,843,188 A | 12/1998 | McDonald |
| 5,891,931 A | 4/1999 | Leboeuf et al. |
| 5,928,282 A | 7/1999 | Nigam |
| 5,964,802 A | 10/1999 | Anello et al. |
| 5,984,962 A | 11/1999 | Anello et al. |
| 6,013,101 A | 1/2000 | Israel |
| 6,015,842 A | 1/2000 | Leboeuf et al. |
| 6,102,539 A | 8/2000 | Tucker |
| 6,117,171 A | 9/2000 | Skottun |
| 6,124,980 A | 9/2000 | Cerbell |
| 6,139,576 A | 10/2000 | Doyle et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,348,437 B1 | 2/2002 | Avery et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,436,092 B1 | 8/2002 | Peyman |
| 6,443,985 B1 | 9/2002 | Woods |
| 6,450,642 B1 | 9/2002 | Jethmalani et al. |
| 6,464,725 B2 | 10/2002 | Skottun |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk, III et al. |
| 6,601,956 B1 | 8/2003 | Jean et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |

| | | |
|---|---|---|
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,060,094 B2 | 6/2006 | Shahinpoor et al. |
| 7,068,439 B2 | 6/2006 | Esch |
| 7,074,227 B2 | 7/2006 | Portney |
| 7,122,053 B2 | 10/2006 | Esch |
| 7,144,423 B2 | 12/2006 | McDonald |
| 7,217,288 B2 | 5/2007 | Esch et al. |
| 7,241,312 B2 | 7/2007 | Lai et al. |
| 7,247,168 B2 | 7/2007 | Esch et al. |
| 7,247,689 B2 | 7/2007 | Makker et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,438,723 B2 | 10/2008 | Esch |
| 7,453,646 B2 | 11/2008 | Lo |
| 7,485,144 B2 | 2/2009 | Esch |
| 7,494,505 B2 | 2/2009 | Kappelhof et al. |
| 7,675,686 B2 | 3/2010 | Lo et al. |
| 7,763,069 B2 | 7/2010 | Brady et al. |
| 7,776,088 B2 | 8/2010 | Shadduck |
| 7,988,292 B2 | 8/2011 | Neal et al. |
| 8,162,927 B2 | 4/2012 | Peyman |
| 2001/0001836 A1 | 5/2001 | Cumming |
| 2001/0016771 A1 | 8/2001 | Cumming |
| 2001/0039449 A1 | 11/2001 | Johnson et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0230203 A1 | 11/2004 | Yaguchi |
| 2005/0021139 A1 | 1/2005 | Shadduck |
| 2005/0113911 A1 | 5/2005 | Peyman |
| 2005/0125000 A1 | 6/2005 | Tourrette et al. |
| 2005/0131535 A1 | 6/2005 | Woods |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0069433 A1 | 3/2006 | Nun |
| 2006/0100703 A1 | 5/2006 | Evans et al. |
| 2006/0116763 A1 | 6/2006 | Simpson |
| 2006/0134173 A1 | 6/2006 | Liu et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0021831 A1 | 1/2007 | Clarke |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0156236 A1 | 7/2007 | Stenger |
| 2007/0203578 A1 | 8/2007 | Scholl et al. |
| 2007/0213817 A1 | 9/2007 | Esch et al. |
| 2007/0244561 A1 | 10/2007 | Ben Nun |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0033449 A1 | 2/2008 | Cole et al. |
| 2008/0046074 A1 | 2/2008 | Smith et al. |
| 2008/0046075 A1 | 2/2008 | Esch et al. |
| 2008/0139769 A1 | 6/2008 | Iwamoto et al. |
| 2008/0200982 A1 | 8/2008 | Your |
| 2008/0269987 A1 | 10/2008 | Barron et al. |
| 2008/0300680 A1 | 12/2008 | Joshua |
| 2008/0306587 A1 | 12/2008 | Your |
| 2008/0306588 A1 | 12/2008 | Smiley et al. |
| 2009/0005865 A1 | 1/2009 | Smiley et al. |
| 2009/0027661 A1 | 1/2009 | Choi et al. |
| 2009/0030425 A1 | 1/2009 | Smiley et al. |
| 2009/0149952 A1 | 6/2009 | Shadduck |
| 2009/0312836 A1 | 12/2009 | Pinchuk et al. |
| 2010/0039709 A1 | 2/2010 | Lo |
| 2010/0131058 A1 | 5/2010 | Shadduck |
| 2010/0179653 A1 | 7/2010 | Argento et al. |
| 2010/0228344 A1 | 9/2010 | Shadduck |
| 2010/0228346 A1 | 9/2010 | Esch |
| 2011/0118834 A1 | 5/2011 | Lo et al. |
| 2012/0078364 A1 | 3/2012 | Stenger |
| 2012/0179249 A1 | 7/2012 | Coleman |
| 2012/0226351 A1 | 9/2012 | Peyman |

FOREIGN PATENT DOCUMENTS

| | | |
|---|---|---|
| JP | 02-167157 | 6/1990 |
| JP | 07-044938 | 5/1995 |
| JP | 9294754 | 11/1997 |
| JP | 10-206609 | 8/1998 |
| JP | 11276509 | 10/1999 |
| SU | 1810052 | 4/1993 |
| WO | WO 97/06751 A | 2/1997 |
| WO | WO 00/41650 A1 | 7/2000 |

| | | |
|---|---|---|
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 7/2002 |
| WO | WO 2004/010895 A2 | 2/2004 |
| WO | WO 2004/046768 A2 | 6/2004 |
| WO | WO 2004/052242 A1 | 6/2004 |
| WO | WO 2004/054471 A3 | 7/2004 |
| WO | WO 2004/072689 A2 | 8/2004 |
| WO | WO 2005/084588 A1 | 9/2005 |
| WO | WO 2006/004707 A2 | 1/2006 |
| WO | WO 2006/047383 A2 | 5/2006 |
| WO | WO 2006/088440 A1 | 8/2006 |
| WO | WO 2007/005529 A2 | 1/2007 |
| WO | WO 2007/030095 A1 | 3/2007 |

OTHER PUBLICATIONS

Scholl et al.; U.S. Appl. No. 13/193,487 entitled "Accommodating Intraocular Lenses," filed Jul. 28, 2011.
Smiley et al.; U.S. Appl. No. 13/193,983 entitled "Accommodating Intraocular Lenses," filed Jul. 29, 2011.
Smiley et al.; U.S. Appl. No. 13/194,004 entitled "Accommodating Intraocular Lenses," filed Jul. 29, 2011.
Hildebrand et al.; U.S. Appl. No. 13/180,427 entitled "Intraocular lens delivery devices and methods of use," filed Jul. 11, 2011.
Baughman et al., "Negative poisson's ratios for extreme states fo matter," Science, vol. 288, pp. 2018-2022, Jun. 16, 2000.
Baughman, "Avoiding the shrink," Nature, vol. 425, pp. 667, Oct. 16, 2003.
Conlisk, A. T. et al; Mass Transfer and Flow in Electrically Charged Micro- and Nano-channels; Analytical Chemistry, vol. 74; iss. 9; pp. 2139-2150; 2002.
Dubbelman et al.; The Thickness of the Aging Human Lens Obtained from Corrected Scheimpflug Images; Optometry & Vison Science; vo. 78; iss. 6; pp. 411-416; Jun. 2001.
Corder, P. F.; Electricity can pump medicine in implanted medical devices; Ohio State Research News; 3 pgs.; May 2, 2002 (printed from internet Aug. 19, 2010).
Gordon, "Applications of shape memory polyurethanes," Proceedings of the First Intl Conf. on Shape Memory and Superelastic Tech., Asilomar Conference Center, Pacific Grove, CA, USA, pp. 115-120, 1994.
Gruber et al.; Exhaustive soxhlet extraction for the complete removal of residual compounds . . . ; Journal of Biomedical Materials Research; vol. 53; No. 5; pp. 445-448; Mar. 2000.
Jeon et al., "Shape memory and nanostructure in poly(norbornyl-POSS) copolymers," Polymer International, vol. 49, pp. 453-457, 2000.
Kim et al., "Polyurethanes having shape memory effects," Polymer, vol. 37, No. 26, pp. 5781-5793, 1996.
Lakes et al., "Dramatically stiffer elastic composite materials due to negative stiffness phase?," Journal of the Mechanics and Physics of Solids, vol. 50, pp. 979-1009, 2002.
Lakes et al., "Extreme damping in composite materials with negative-stiffness inclusions," Nature, vol. 410, pp. 565-567, Mar. 29, 2001.
Lakes et al., "Microbuckling instability in elastomeric cellular sollids," J. Materials Science, vol. 28, pp. 4667-4672, 1993.
Lakes, "A broader view of membranes," Nature, vol. 414, pp. 503-504, Nov. 29, 2001.
Lakes, "Extreme damping in compliant composites with a negative-stiffness phase," Philosophical Magazine Letters, vol. 81, No. 2, pp. 95-100, 2001.
Lakes, "Extreme damping in composite materials with a negative stiffness phase," Physical Review Letters, vol. 86, No. 13, pp. 2897-2900, Mar. 26, 2001.
Lakes, "Lateral deformations in extreme matter," Science, vol. 288, pp. 1976, Jun. 2000; 3 pgs.
Lakes, "Negative poisson's ratio materials," Science, vol. 238, pp. 551, Oct. 23, 1987.
Lakes, "No contractile obligations," Nature, vol. 358, pp. 713-714, 1992.
Lendlein et al., "Biodegradable, elastic shape-memory polymers for potential biomedical applications", Science; vol. 296; pp. 1673-1676; May 31, 2002.
Lendlein et al., "Shape-memory polymers," Angew. Chem. Int. Ed.; vol. 41; pp. 2034-2057; 2002.
Li et al., "Crystallinity and morphology of segmented polyurethanes with different soft-segment length," Journal of Applied Polymer Science, vol. 62, pp. 631-638, 1996.
Liu et al., "Thermomechanical characterization of a tailored series of shape memory polymers," Journal of Applied Medical Polymers, vol. 6, No. 2, 2002.
Mather et al., "Strain recovery in POSS hybrid thermoplastics," Polymer Preprints, vol. 41, No. 1, pp. 528-529, 2000.
Metcalfe et al., "Cold hibernated elastic memory foams for endovascular interventions," Biomaterials, vol. 24, pp. 491-497, 2003.
Takahashi et al., "Structure and properties of shape-memory polyurethane block copolymers," Journal of Applied Polymer Science, vol. 60, pp. 1061-1069, 1996.
Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.
Tobushi et al., "Thermomechanical properties of shape memory polymers of polyurethane series and their applications," Journal de Physique IV, Colloque C1, vol. 6, pp. 377-384, 1996.
Vass et al.; Prediction of pseudophakic capsular bag diameter based on biometric variables; J Cataract Refract Surg.; vol. 25; pp. 1376-1381; 1999.
Wang et al., "Deformation of extreme viscoelastic metals and composites," Materials Science and Enginerring A, vol. 370, pp. 41-49, 2004.
Wang et al., "Extreme stiffness systems due to negative stiffness elements," American Journal of Physics, vol. 72, No. 1, pp. 40-50, Jan. 2004.
Wang et al., "Stable extremely-high-damping discrete viscoelastic systems due to native stiffness elements," Applied Physics Letters, vol. 84, No. 22, pp. 4451-4453, May 31, 2004.
Wyant et al; "Basic Wavefront Aberration Theory for Optical Metrology," Applied Optics and Optical Engineering, vol. XI, 1992: pp. 1, 28-39.
Xu et al., "Basic negative poisson's ratio microstructures by soft lithography," Advanced Materials, vol. 11, No. 14, 1999, pp. 1186-1189, 1999.
Shadduck, John H.; U.S. Appl. No. 12/852,733 entitled "Intraocular Lens System and Method for Power Adjustment," filed Aug. 9, 2010.
Hildebrand et al.; U.S. Appl. No. 12/872,314 entitled "Lens Capsule Size Estimation," filed Aug. 31, 2010.
Shadduck, John H.; U.S. Appl. No. 13/300,245 entitled "Accommodating Intraocular Lenses and Methods of Use," filed Nov. 18, 2011.
Matthews, Gregory V.; U.S. Appl. No. 13/427,617 entitled "Intraocular Lens Loading Systems and Methods of Use," filed Mar. 22, 2012.
USPTO, "Office Action," corresponding U.S. Appl. No. 12/782,639, mailed on Jan. 9, 2012, 33 pages.

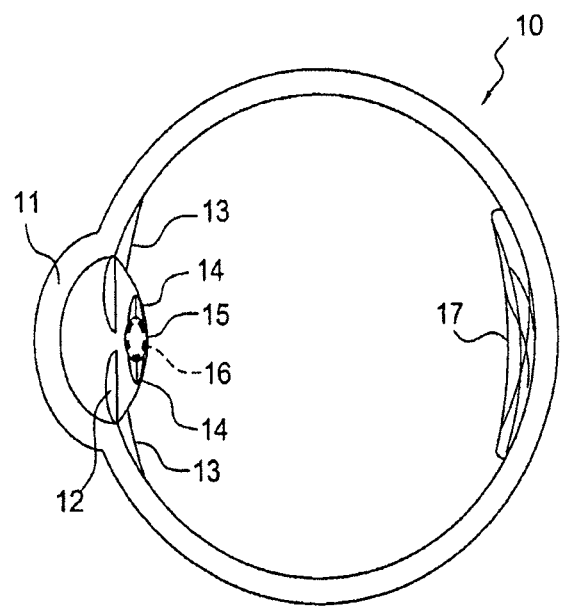
FIG. 1
FIG. 2A
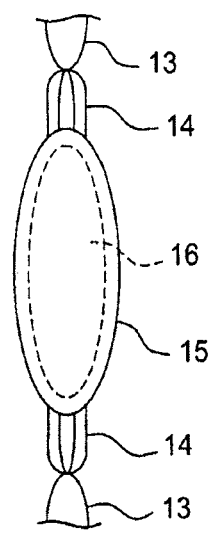
FIG. 2B
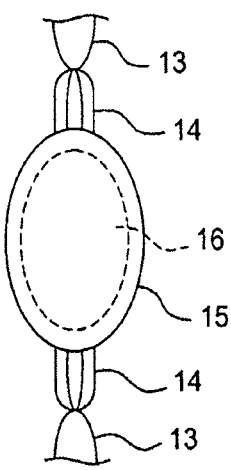

ACCOMMODATING INTRAOCULAR LENS HAVING PERIPHERALLY ACTUATED DEFLECTABLE SURFACE AND METHOD

CROSS-REFERENCE

This application is a continuation of U.S. application Ser. No. 11/715,221, filed Mar. 6, 2007; which is a continuation of U.S. application Ser. No. 11/252,916 filed Oct. 17, 2005, now U.S. Pat. No. 7,217,288; which is a continuation-in-part of U.S. application Ser. No. 10/971,598, filed Oct. 22, 2004, now U.S. Pat. No. 7,261,737; which is a continuation-in-part of U.S. application Ser. No. 10/734,514, filed Dec. 12, 2003, now U.S. Pat. No. 7,122,053; which claims the benefit of priority from U.S. Provisional Application No. 60/433,046, filed Dec. 12, 2002; all of which are incorporated by reference in their entirety as if fully set forth herein.

BACKGROUND OF THE INVENTION

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens (IOL) implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age-related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. Since the lens can no longer accommodate, however, the patient typically needs glasses for reading.

More specifically, the imaging properties of the human eye are facilitated by several optical interfaces. A healthy youthful human eye has a total power of approximately 59 diopters, with the anterior surface of the cornea (e.g. the exterior surface, including the tear layer) providing about 48 diopters of power, while the posterior surface provides about −4 diopters. The crystalline lens, which is situated posterior of the pupil in a transparent elastic capsule supported by the ciliary muscles, provides about 15 diopters of power, and also performs the critical function of focusing images upon the retina. This focusing ability, referred to as "accommodation," enables imaging of objects at various distances.

The power of the lens in a youthful eye can be adjusted from 15 diopters to about 29 diopters by adjusting the shape of the lens from a moderately convex shape to a highly convex shape. The mechanism generally accepted to cause this adjustment is that ciliary muscles supporting the capsule (and the lens contained therein), move between a relaxed state (corresponding to the moderately convex shape) to a contracted state (corresponding to the highly convex shape). Because the lens itself is composed of viscous, gelatinous transparent fibers, arranged in an "onion-like" layered structure, forces applied to the capsule by the ciliary muscles cause the lens to change shape.

Isolated from the eye, the relaxed capsule and lens take on a spherical shape. Within the eye, however, the capsule is connected around its circumference by approximately 70 tiny ligament fibers to the ciliary muscles, which in turn are attached to an inner surface of the eyeball. The ciliary muscles that support the lens and capsule therefore are believed to act in a sphincter muscular mode. Accordingly, when the ciliary muscles are relaxed, the capsule and lens are pulled about the circumference to a larger diameter, thereby flattening the lens, whereas when the ciliary muscles are contracted, the lens and capsule relax somewhat and assume a smaller diameter that approaches a more spherical shape, thereby increasing the diopter power of the lens.

As noted above, the youthful eye has approximately 14 diopters of accommodation. As a person ages, the lens hardens and becomes less elastic, so that by about age 45-50, accommodation is reduced to about 2 diopters. At a later age the lens may be considered to be non-accommodating, a condition know as "presbyopia". Because the imaging distance is fixed, presbyopia typically entails the need for bi-focals to facilitate near and far vision.

Apart from age-related loss of accommodation ability, such loss is innate to the placement of IOLs for the treatment of cataracts. IOLs are generally single element lenses made from a suitable polymer material, such as acrylics or silicones. After placement, accommodation is no longer possible, although this ability is typically already lost for persons receiving an IOL. There is significant need to provide for accommodation in IOL products so that IOL recipients will have accommodating ability.

Although previously known workers in the field of accommodating IOLs have made some progress, the relative complexity of the methods and apparatus developed to date have prevented widespread commercialization of such devices. Previously known devices have proved too complex to be practical to construct or have achieved only limited success, due to the inability to provide accommodation of more than 1-2 diopters.

U.S. Pat. No. 5,443,506 to Garabet describes an accommodating fluid-filled lens wherein electrical potentials generated by contraction of the ciliary muscles cause changes in the index of refraction of fluid carried within a central optic portion. U.S. Pat. No. 4,816,031 to Pfoff discloses an IOL with a hard PMMA lens separated by a single chamber from a flexible thin lens layer that uses microfluid pumps to vary a volume of fluid between the PMMA lens portion and the thin layer portion and provide accommodation. U.S. Pat. No. 4,932,966 to Christie et al. discloses an intraocular lens comprising a thin flexible layer sealed along its periphery to a support layer, wherein forces applied to fluid reservoirs in the haptics vary a volume of fluid between the plurality of layers to provide accommodation.

Although fluid-actuated mechanisms such as described in the aforementioned patents have been investigated, commercially available accommodating lenses, such as developed by Eyeonics, Inc. of Aliso Viejo, Calif., rely on ciliary muscle contraction of the IOL haptics to vault the optic towards or away from the retina to adjust the focus of the device.

One promising line of IOL apparatus and methods is disclosed in commonly assigned U.S. Patent Publication 2005/0119740 A1 to Esch et al. There, apparatus and methods are described in which a patient's vision may be improved by implantation of an IOL having one or more pistons disposed at or near the center of a deformable surface of the IOL. Due to the potential for reflections to arise during movement of the piston near the optical axis of the IOL, it may be desirable to relocate the actuators to a peripheral portion of the IOL.

In view of the foregoing, it would be desirable to provide apparatus and methods that restore appropriate optical focusing power action to the human eye.

It further would be desirable to provide methods and apparatus wherein a dynamic lens surface may be effectively manipulated by the ciliary muscular mechanisms within the eye.

It still further would be desirable to provide methods and apparatus that utilize pressure applied by the accommodating muscular action to deform an optical surface of the IOL. In particular, it would be desirable to provide an IOL in which muscular pressure may be applied through one or more actuators to obtain a mechanical advantage.

It is yet further desirable to provide methods and apparatus that reduce the possibility of reflections within the IOL arising due to movement of mechanical actuators situated along or near the optical axis of the IOL.

SUMMARY OF THE INVENTION

In view of the foregoing, it is an object of the present invention to provide apparatus and methods that restore appropriate optical focusing power action to the human eye.

It is a further object of this invention to provide methods and apparatus wherein a dynamic lens surface may be effectively manipulated by the ciliary muscular mechanisms within the eye.

It is another object of the present invention to provide methods and apparatus that utilize pressure applied by the accommodating muscular action to deform an optical surface of the IOL.

It is a further object of this invention to provide methods and apparatus for applying muscular pressure, through one or more actuators, to obtain a mechanical advantage in altering the optical parameters of one or more surfaces of the IOL.

It is yet a further object of this invention to provide methods and apparatus that reduce the possibility of reflections within the IOL arising due to movement of mechanical actuators situated along or near the optical axis of the IOL.

These and other objects of the present invention are accomplished by providing a lens in which force exerted on a fluid reservoir by the movement of the ciliary muscles, zonules and capsule is applied to a dynamic optical surface.

In accordance with the principles of the invention, an IOL is provided having a dynamic lens surface that deflects in response to forces applied to one or more haptics. In a preferred embodiment, the deformable surface is anchored to a substrate near the optical axis of the IOL, and is deformed from an accommodated state to an unaccommodated state by deflection of the periphery of the deformable surface. In this manner, the IOL of the present invention reduces the possibility that light entering the IOL may be reflected due to movement of an actuator disposed at or near the optical axis of the IOL.

In accordance with another aspect of the present invention, a reservoir containing a fluid is disposed in a haptic portion of the IOL, so that compressive forces arising due to movement of the ciliary muscles are transmitted via the haptic portion and fluid to deform the dynamic surface, thereby varying the accommodation of the IOL.

Methods of using the lens of the present invention also are provided.

INCORPORATION BY REFERENCE

All publications and patent applications mentioned in this application are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a sectional side view of a human eye;

FIGS. 2A and 2B are, respectively, detailed sectional side views of the lens and supporting structures of FIG. 1 illustrating relaxed and contracted states of the ciliary muscles;

DETAILED DESCRIPTION OF THE INVENTION

Figure 3A:
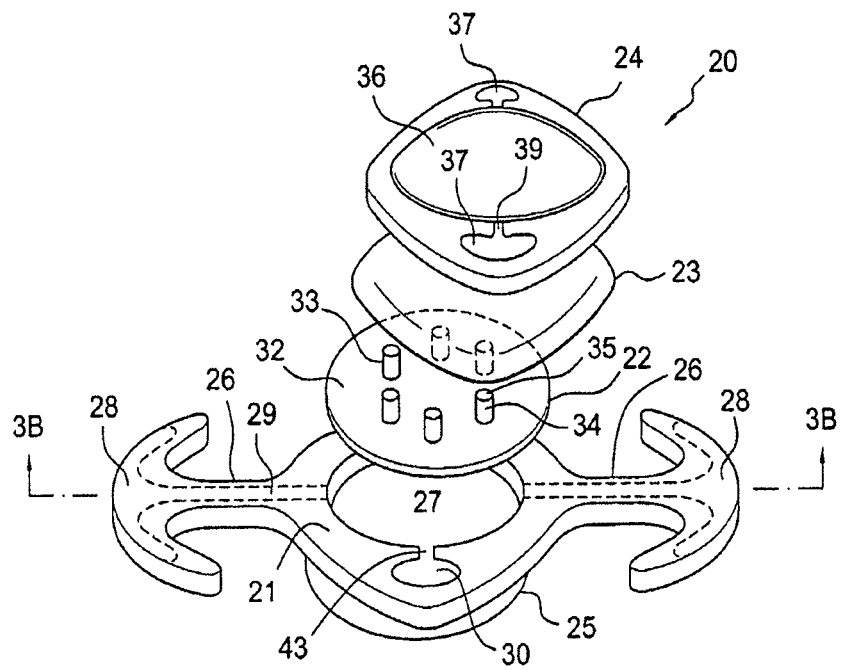
FIGS. 3A and 3B are, respectively, an exploded perspective and side sectional view taken along line 3B-3B of an exemplary embodiment of an accommodating intraocular lens described in U.S. Patent Publication 2004/0169816 A1.

The present invention is directed to an in-situ accommodating intraocular lens system. In accordance with the principles of the present invention, methods and apparatus are provided wherein a lens has an optic element comprising a deformable surface and an actuator that selectively deflects the deformable surface to change an optical power of the lens. In accordance with the principles of the present invention, a central portion of the deformable surface is anchored to a substrate and the lens transitions between the accommodated and unaccommodated positions by deflection of a peripheral region of the deformable surface.

Referring to FIGS. 1 and 2, the structure and operation of a human eye are first described as context for the present invention. Eye 10 includes cornea 11 pupil 12, ciliary muscles 13, ligament fibers 14, capsule 15, lens 16 and retina 17. Natural lens 16 is composed of viscous, gelatinous transparent fibers, arranged in an "onion-like" layered structure, and is disposed in transparent elastic capsule 15. Capsule 15 is joined by ligament fibers 14 around its circumference to ciliary muscles 13, which are in turn attached to the inner surface of eye 10.

Isolated from the eye, the relaxed capsule and lens takes on a spherical shape. However, as described hereinabove, when suspended within the eye by ligament fibers 14, capsule 15 moves between a moderately convex shape (when the ciliary muscles are relaxed) to a highly convex shape (when the ciliary muscles are contracted). As depicted in FIG. 2A, when ciliary muscles 13 relax, capsule 15 and lens 16 are pulled about the circumference, thereby flattening the lens. As depicted in FIG. 2B, when ciliary muscles 13 contract, capsule 15 and lens 16 relax somewhat, thus allowing the lens and capsule to assume a more spherical shape, and thus increasing the diopter power of the lens.

As discussed hereinabove, commercially available accommodating lenses, such as the Crystalens device by Eyeonics, Inc., Aliso Viejo, Calif., typically involve converting diametral movements of the ciliary muscle into forward and backward movement of the optic portion of the IOL relative to the retina. This approach is thought to be required because, following extraction of a cataract-effected lens, the capsular bag is very loose, and the ligament fibers that couple the capsule to the ciliary muscles are no longer in tension. Devices such as the Crystalens thus do not employ the natural accommodation mechanisms described above, but instead rely directly on radially inward compressive forces applied by the ciliary muscle to the haptics of the IOL.

In accordance with principles of the present invention, compressive forces applied to the haptics of the IOL are employed to provide accommodation by deflecting a dynamic surface of the lens. This deflection causes a variation in the optical path of light passing through the lens, thus altering its optical parameters.

Figure 3B:
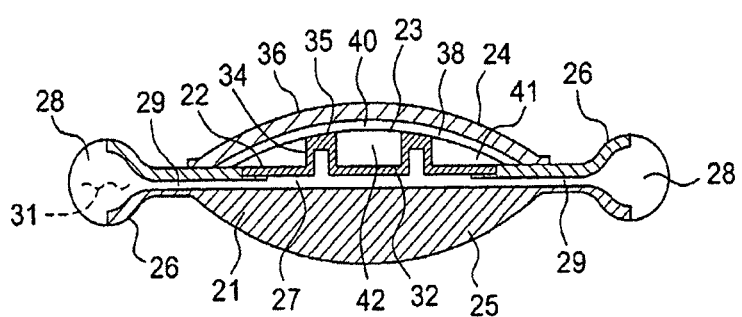

Referring now to FIGS. 3A and 3B, an embodiment of the accommodating IOL of U.S. Patent Publication No. 2004/0169816 A1 is described. In that device, a flexible layer situated between two fluids of different indices of refraction is deflected to vary the accommodating power of the lens. IOL 20 comprises substrate 21, actuator element 22, flexible layer 23 and anterior element 24, assembled in a sandwiched configuration.

Substrate 21 preferably comprises a sturdy transparent polymer and includes posterior lens 25, haptics 26, lower chamber 27, reservoirs 28, passageways 29 and lower relief reservoirs 30. Lower chamber 27 communicates with reservoirs 28 disposed on the ends of haptics 26 via passageways 29. Lower chamber 27, reservoirs 28, passageways 29 and lower relief reservoirs 30 are filled with transparent fluid 31. The outwardly directed surfaces of haptics 26 comprise a resilient elastic material that permits force applied to those surfaces by the ciliary muscles to cause fluid to move from reservoirs 28 through passageways 29 into lower chamber 27.

Actuator element 22 comprises disk-shaped member 32 having a plurality of cells 33 extending upwardly from its upper surface. Each cell 33 illustratively comprises an annular sidewall 34 and top 35. The relative thicknesses of member 32 and sidewalls 34 and tops 35 are selected so that when pressurized fluid is introduced into lower chamber 27, tops 35 of cells 33 extend axially upward. Illustratively, cells 33 are arranged in a ring at a predetermined radius from the optical axis of lens 20, although more or fewer cells 33 may be employed, and their location selected to enhance deflection of layer 23, as described hereinbelow.

Anterior element 24 preferably comprises a rigid transparent material, and includes anterior lens 36, and upper relief reservoirs 37. The interior surface of anterior element 24 is convex and forms upper chamber 38, which accommodates upward motion of flexible layer 23, as described hereinbelow. Upper relief reservoirs 37 are disposed in alignment with lower relief chambers 30 in substrate 21, outside the optical path of anterior lens 24. Upper chamber 38 communicates with upper relief reservoirs 37 via passageways 39, and is filled with transparent fluid 40.

Flexible layer 23 is affixed around its circumference to substrate 21 and is disposed in contact with tops 35 of cells 33. Transparent fluid 41 is contained within space 42 between the upper surface of actuator element 22 and lower surface of layer 23. Lower relief reservoirs 30 communicate with space 42 via passageways 43 disposed in substrate 21. A portion of layer 23 divides upper relief reservoirs 37 from lower relief reservoirs 30, for purposes to be described hereinafter. Fluid 41 disposed in space 42, preferably has the same index of refraction as fluid 41 in lower chamber 27, and a different index of refraction than fluid 40 contained in upper chamber 38.

When assembled as shown in FIG. 3B and implanted into the empty capsule of a cataract patient, compressive forces applied by the ciliary muscles cause fluid 31 to move from reservoirs 28 into lower chamber 27, thereby causing tops 35 of cells 33 to extend axially upward. Upward movement of tops 35 of cells 33 in turn causes layer 23 to deflect upward and displace fluid 40 in upper chamber 38. Fluid displaced from upper chamber 38 flows into upper relief reservoirs 37 via passageways 39.

Simultaneously, because lower relief reservoirs 30 communicate with space 42, fluid 41 is drawn from lower relief reservoirs 30 as layer 23 is deflected upward by cells 33. Consequently, the portions of layer 23 that divide upper relief reservoirs 37 from lower relief reservoirs 30 serve as diaphragms that permit fluid to be simultaneously displaced into one reservoir and withdrawn from the other. This enables fluids 40 and 41 to pass freely in and out of the optical space in order to balance relative volumes of fluid, the total volume of fluids 40 and 41 remaining constant.

Movement of layer 23, and the accompanying displacement of volumes of fluid 40 in upper chamber 38 with a corresponding volume of fluid 41 of a different index of fraction in space 42, changes the optical parameters of the lens, thereby moving the focus of the lens from near to far or vice-versa. Posterior lens 25, which in this case comprises a solid material, also provides additional optical power. Posterior lens 25 also may provide optical index dispersion so as to optimize aberration characteristics, including wave aberration of all order, or chromatic aberration.

When the ciliary muscles relax, tops 35 of cells 33 contract, and layer 23 resiliently contracts to its original position. This in turn forces excess fluid 41 in space 42 back into lower relief reservoirs 30. In addition, as the pressure in upper chamber 38 is reduced, fluid 40 is drawn out of upper relief reservoirs 37 and into upper chamber 38.

In the embodiment of FIG. 3, fluid 31 is forced into cell 33 by ciliary forces acting on the surface of reservoir 28, so that the actuator works in a direction parallel to the optical axis of the lens. As will be appreciated, actuator element 22 must be index matched to fluid 31, which moves with cells 33, as well as fluid 41 that surrounds cells 33 in space 42. Also in the embodiment of FIG. 3, posterior lens 25 is formed from the same material as substrate 21. Alternatively, posterior lens 25 may comprise a different material than substrate 21, having a shape and optical parameters chosen to optimize the optical performance of the lens system.

Relevant to the IOL of the present invention, cells 33 of the device depicted in FIG. 3 act not only to deflect layer 23, but also serve as fulcrum contact points. This effect is described generally with respect to FIGS. 4A-4C, wherein the effect of the placement of the fulcrum contact points is described. Generally, fixation within the optical zone of surface 50 (corresponding to flexible layer 23 of the embodiment described hereinabove), may be accomplished in several fashions depending on the effect and efficiency required of the fluid forces provided by the fluid being moved into the chamber or cell by the forces acting on the reservoirs in the IOL haptics.

If it is desired that surface 50 assume a flatter configuration 50' that provides less optical focusing power (shown in dotted line in FIG. 4A), then fixation at fulcrum point 51 would be desired. If, on the other hand, it is desired that surface 50 provide more power when the ciliary muscles contract (corresponding to highly convex configuration 50", shown in dotted line in FIG. 4B), then fixation at fulcrum points 52 would be desirable.

As a further alternative, to obtain most efficient use of fluid power, e.g., to obtain maximal change in optical power for a given movement of surface 50 (corresponding to surface configuration 50''' in FIG. 4C), some fixation at some intermediate fulcrum point 53 may be desired. Fulcrum point 53 also may be selected so as to minimize the change in the volumes of the total fluid within the optical zone, thereby obviating the need for relief reservoirs to absorb excess fluid volumes. In this latter case, deflection of the flexible layer causes sufficient redistribution of the fluids within the first and second chambers to alter the power of the lens.

The foregoing discussion of fulcrum points may be advantageously employed not only in a two fluid system as described in U.S. Patent Publication No. 2004/0169816 A1, but also in a system such as described in commonly assigned U.S. Patent Publication No. 2005/0119740. In the accommodating IOL described in that application, one or more actuators disposed near the optical axis of a deformable lens element are employed to transition the lens between accommodated and unaccommodated states.

In accordance with the principles of the present invention, the fulcrum concepts discussed above with respect to FIGS. 4A-4C are applied to a lens system similar to that of U.S. Patent Publication No. 2005/0119740 A1 to reduce the potential for reflections to arise from movement of the actuator disposed near the optical axis of the IOL. In particular, the actuators are moved to the periphery of the deformable lens element, while the center of the dynamic surface, along the optical axis of the IOL, is anchored to the lens substrate.

Referring now to FIGS. 5A-5D, a first embodiment of an IOL constructed in accordance with the principles of the present invention is described. IOL 60 is similar in design to the IOL of U.S. Patent Publication No. 2005/0119740 A1, except that in IOL 60 the actuators are disposed at the periphery of the anterior lens element. IOL 60 operates in the manner described for the dynamic surface of FIG. 4A, with its anterior lens element anchored to the lens substrate. Actuation of the actuators disposed at the periphery of the anterior lens element lift the edges of the lens element, thereby flattening the surface and reducing accommodation of the IOL. Conversely, lowering of the periphery of the anterior lens increases convexity and accommodation of IOL 60.

As will be explained more fully below, IOL 60 assumes an accommodated position in its relaxed state, i.e., when no outside forces are acting on it. After implantation in a patient's eye, the IOL assumes the accommodated configuration when the ciliary muscles contract and the capsule relaxes. In contrast, when the ciliary muscles relax and the capsule is pulled taut, forces applied by the capsule to the haptic cause the IOL to transition to the unaccommodated state.

IOL 60 comprises optic portion 61 and haptic portion 62. Optic portion 61 includes anterior lens element 63, substrate 64 and posterior lens surface 65. Haptic portion 62 illustratively comprises four deformable tubular members 66 mounted on extensions 67 projecting from substrate 64. It should be understood that the invention may be practiced with more or less tubular members than shown in FIG. 5.

Substrate 64 preferably comprises a sturdy transparent polymer illustratively has posterior lens surface 65 integrally formed thereon. Anterior lens element 63 is coupled to the center of substrate 64 by anchor 68, while the periphery of the lens element is sealed to the edge of substrate 64 by sidewall 69. Anterior lens element 63 also includes a flexible circular partition 70 coupled to the substrate to define annular chamber 71. Space 72 defined by anterior lens element 63 and substrate 64 inward of partition 70 preferably is filled with fluid 73, such as a silicone oil, having a refractive index that matches the surrounding components of optic portion 61.

Substrate 64 includes one or more relief reservoirs 74 disposed near the periphery of posterior lens surface 65 that communicate with space 72 via channels 75. Substrate 64 further includes peripheral passageway 76 that communicates with annular chamber 71 and the interior of tubular members 66 via passageways 77. The interior of tubular members 66, annular chamber 71, peripheral passageway 76 and passageways 77 all are filled with fluid 78 having an index of refraction matched to the surrounding components. Fluid 78 preferably, but need not be, the same as fluid 73 in space 72.

Tubular members 66 include flexible fluid-tight endcaps 79 and are attached to extensions 67 of substrate 64 using a suitable biocompatible adhesive, thermal bonding, or other methods known in the art. Tubular member 66 preferably has a substantially circular cross-section in the relaxed state, i.e., when no forces are acting on it. The tubular members of haptic portion 62 are configured so that forces applied by the capsule to the anterior and posterior faces of the tubular members causes the tubular members to transition to an ellipsoidal shape, thereby inducing fluid 78 to flow through passageways 77 and into annular chamber 71 via peripheral passageway 76. When the lateral forces applied to the tubular member subside, for example, when the capsule becomes loose as a consequence of ciliary muscle contraction, tubular members 66 return to their unstressed shapes, causing fluid to flow from annular chamber 71 back to the interior of the tubular members.

Figure 4A:
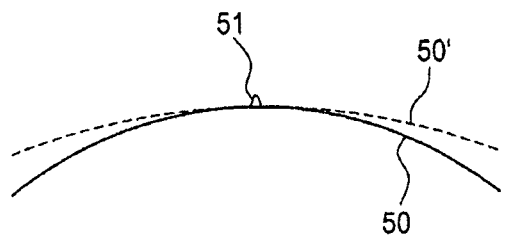
FIGS. 4A-4C are schematic views of illustrating the use of fulcrum points to facilitate deflection of an optical surface as described in U.S. Patent Publication 2004/0169816 A1.
Figure 4B:
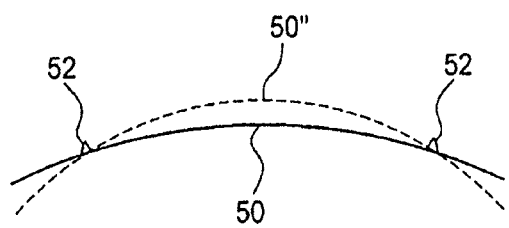
Figure 4C:
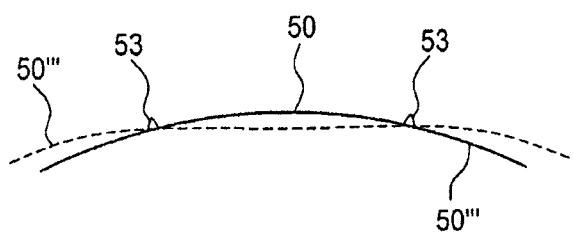
Figure 5A:
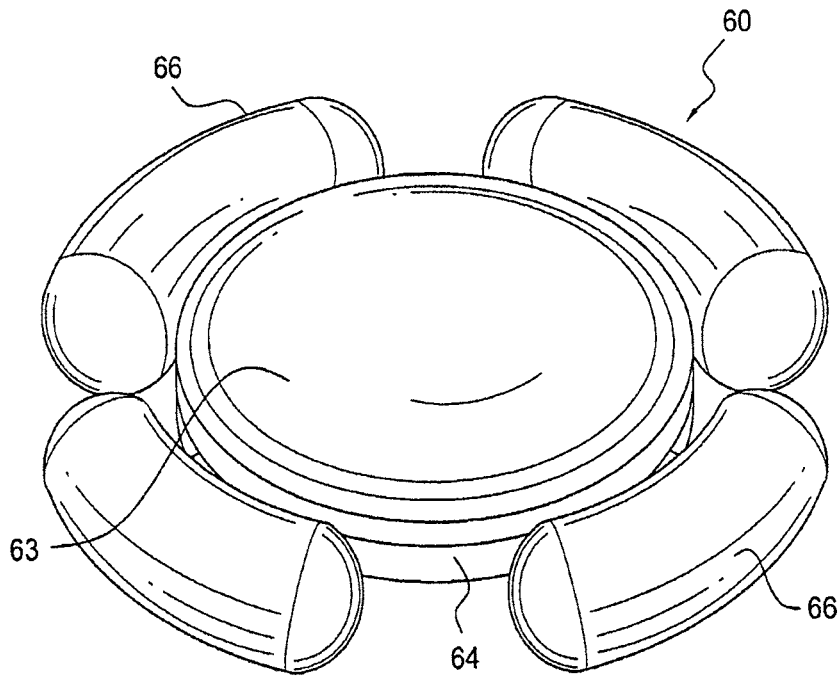
FIGS. 5A-5D are, respectively, a perspective view, a top view, a cross-sectional perspective view taken along line 5C-5C, and an exploded perspective view of an embodiment of an accommodating intraocular lens of the present invention.
Figure 5B:
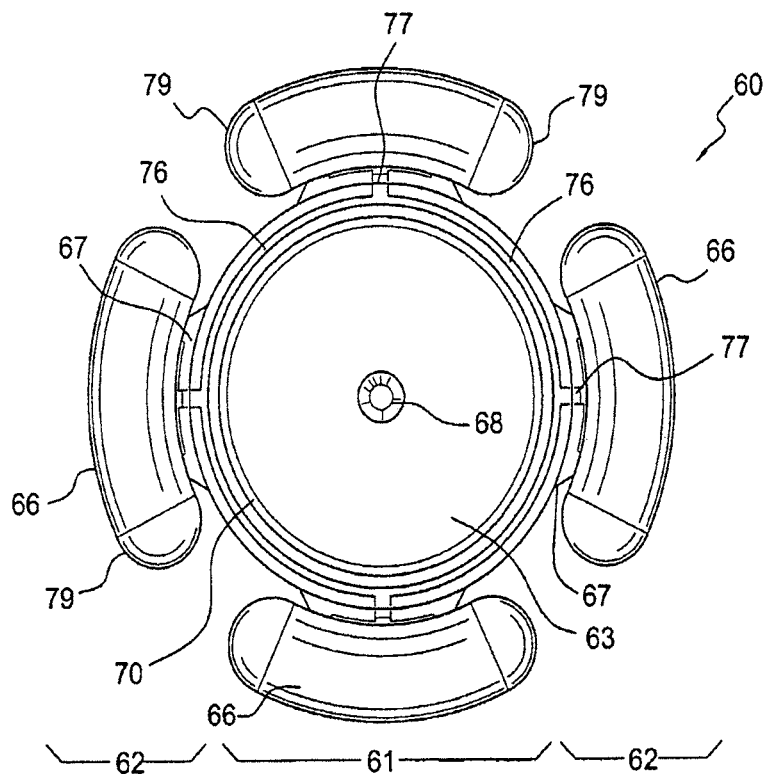
Figure 5C:
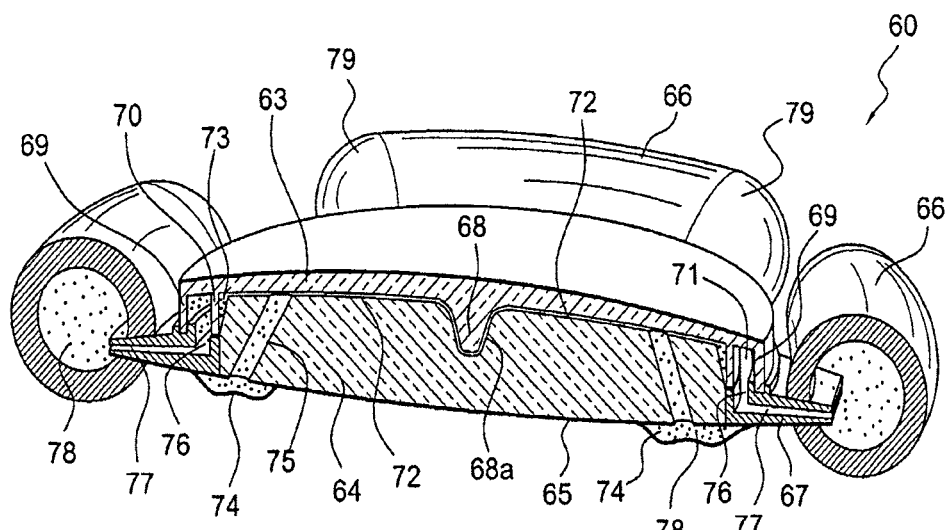
Figure 5D:
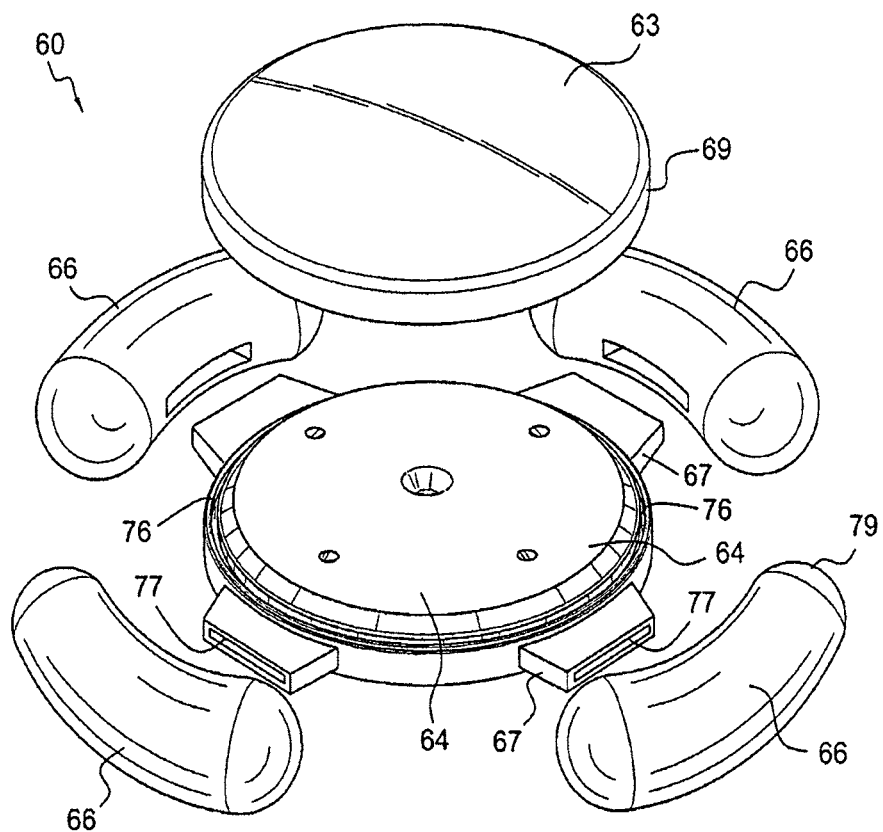

In accordance with the principles of the present invention, anchor 68 serves as the function of fulcrum point 51 of FIG. 4A, while annular chamber 71 serves as actuator. When fluid moves from the haptic portion 62 to annular chamber 71, the periphery of the anterior lens element lifts upwards, thereby flattening the lens surface and reducing the diopter power of the lens. To account for the increase in volume in space 72 resulting from lifting of the edges of anterior lens element 73, fluid 78 is drawn from flexible reservoirs 74 into space 72 via passageways 75. Likewise, when the lens moves to its accommodated state, fluid 78 moves through passageways 75 back to flexible reservoirs 74.

In operation, when implanted in an eye, tubular members 66 of haptic portion 62 have a substantially circular shape when the ciliary muscles are contracted. This corresponds to the maximum volume of the interior of tubular members 66 and the minimum volume of fluid 73 in annular chamber 71. When the ciliary muscles relax, the capsule is pulled taut by the zonules and applies compressive forces to the anterior and posterior surfaces of tubular members 66. This causes the tubular members to deform to a non-circular cross-section, thereby squeezing fluid into annular chamber 71. Sidewall 69 and partition 70 expand responsive to the increased volume in annular chamber 71, thereby lifting the edge of anterior lens element 63. The increased volume of space 72 arising from this movement is made up by transfer of fluid 78 from flexible reservoirs 74 to space 72 via passageways 75. These actions result in IOL 60 assuming a less accommodated configuration.

When the ciliary muscles relax, tubular members 66 are no longer subjected to lateral compressive forces, and return to their unstressed geometry. This in turn reduces the volume of fluid in annular chamber 71, causing sidewall 69 and partition 70 to return to their undeformed shapes, thereby increasing the convexity of anterior lens element 63. Fluid 82 is likewise forced from space 72 between anterior lens element 63 and substrate 64, through passageway 75 and back into flexible reservoirs 74. IOL 60 thus returns to its accommodated configuration.

IOL 60 may be manufactured as described above with predetermined volumes of fluids 73 and 78. Alternatively, tubular members 66 and/or flexible reservoirs may comprise a semi-permeable osmotic material and IOL manufactured to contain smaller amounts of fluids 73 and 78 than may be desired for operation of the IOL. In this alternative embodiment, IOL 60 may be implanted in a slightly collapsed state, thereby facilitating insertion. Subsequently, the osmotic gradient may cause water in the eye to permeate the tubular member and/or flexible reservoirs to increase the volume of fluids 73 and 78 to provide correction functioning of IOL 60.

Referring now to FIG. 6, an alternative embodiment of an IOL of the present invention is described. Like the embodiment of FIG. 5, IOL 80 also has the center of the anterior lens element fixed to the substrate, so that the edges of the lens element lift to transition the IOL to the unaccommodated state.

IOL 80 assumes an accommodated position when no outside forces are acting on it. After implantation in a patient's eye, the IOL assumes the accommodated configuration when the ciliary muscles contract. In contrast, when the ciliary muscles relax and the capsule is pulled taut by the zonules, the capsule applies forces to the haptic portion of the IOL, which in turn causes the IOL to transition to the unaccommodated state.

IOL 80 comprises optic portion 81 and haptic portion 82. Optic portion 81 shapes and focuses light on the optic nerve while haptic portion 82 orients and supports the IOL with the capsule and actuates the accommodating mechanism of the IOL. As depicted in FIG. 6C, IOL 80 illustratively comprises anterior portion 83 affixed to posterior portion 84.

Anterior portion 83 comprises a flexible optically transparent material that forms anterior lens element 85. Anterior lens element 85 includes anchor 86 that extends posteriorly from the center of the lens element 85. Lens element 85 is coupled around its edge 87 to haptic half 88 by flexible membrane 89. Spacers 90 also extend posteriorly from the interior surface of anterior portion 83. Posterior portion 84 comprises sturdy optically transparent polymer substrate 91, posterior lens surface 92 and posterior haptic half 93, peripheral step 94 and receptacle 95.

Figure 6A:
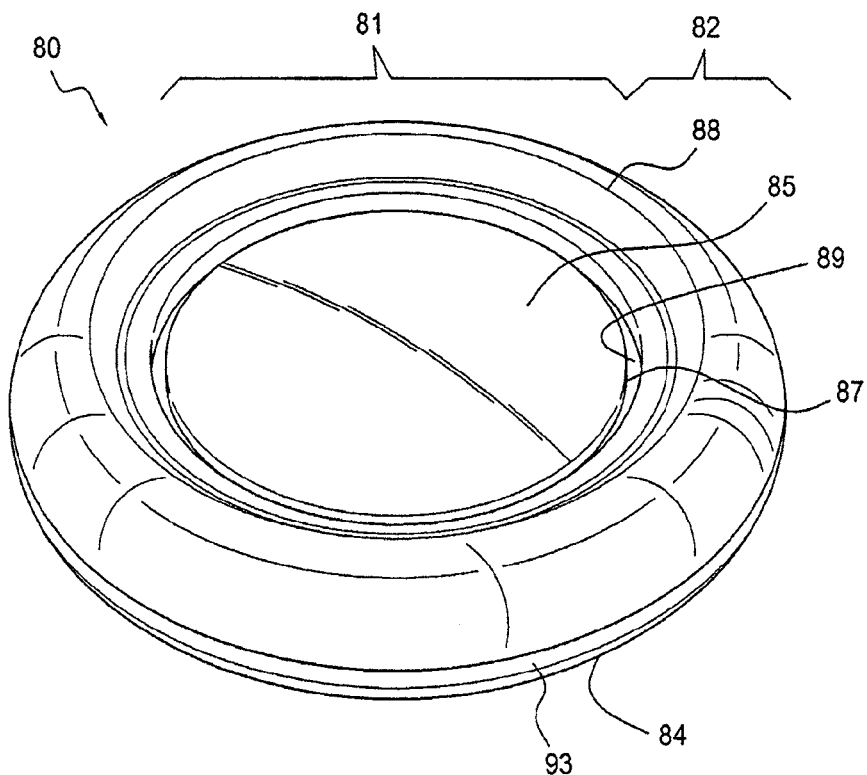
FIGS. 6A-6D are, respectively, a perspective view, a cross-sectional perspective view taken along line 6B-6B, an exploded perspective view, and a top transparent view of an alternative embodiment of an accommodating intraocular lens of the present invention.
Figure 6B:
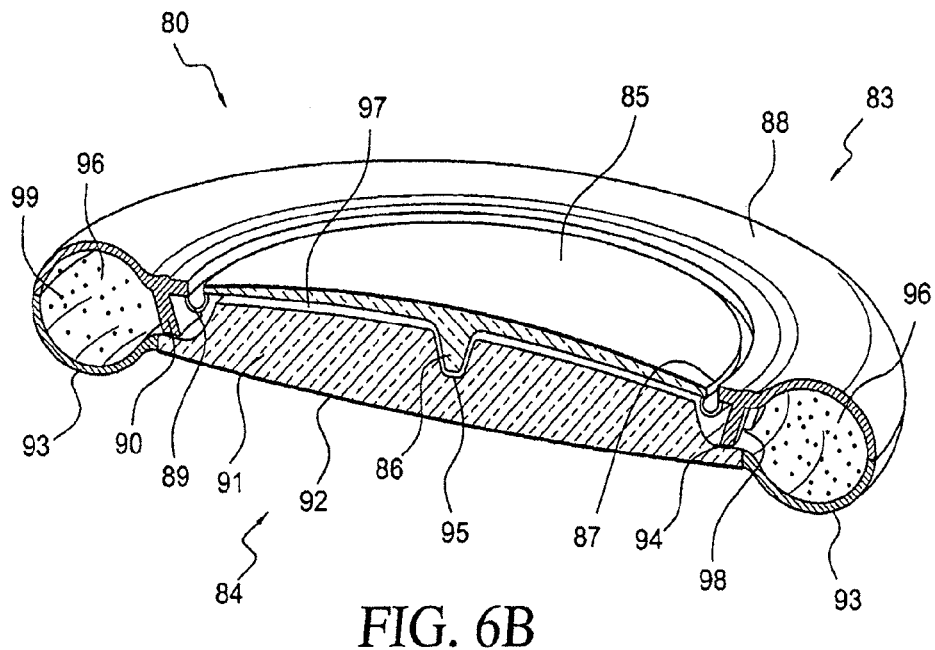
Figure 6C:
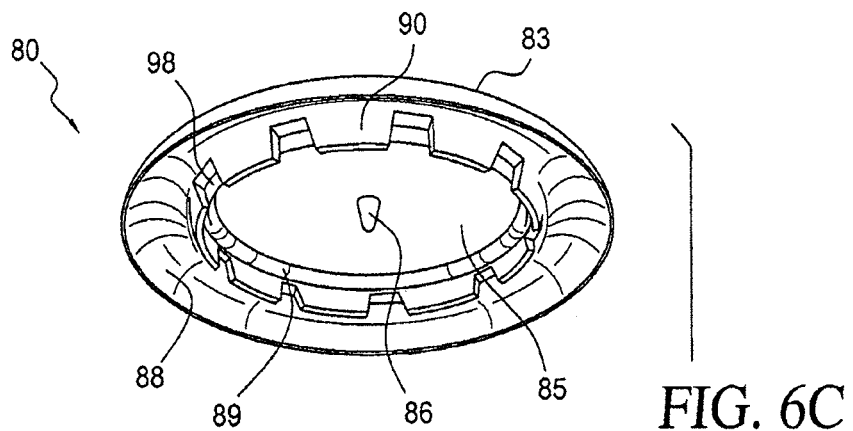
Figure 6C:
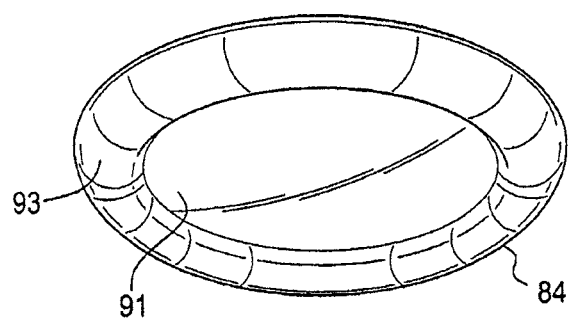
Figure 6D:
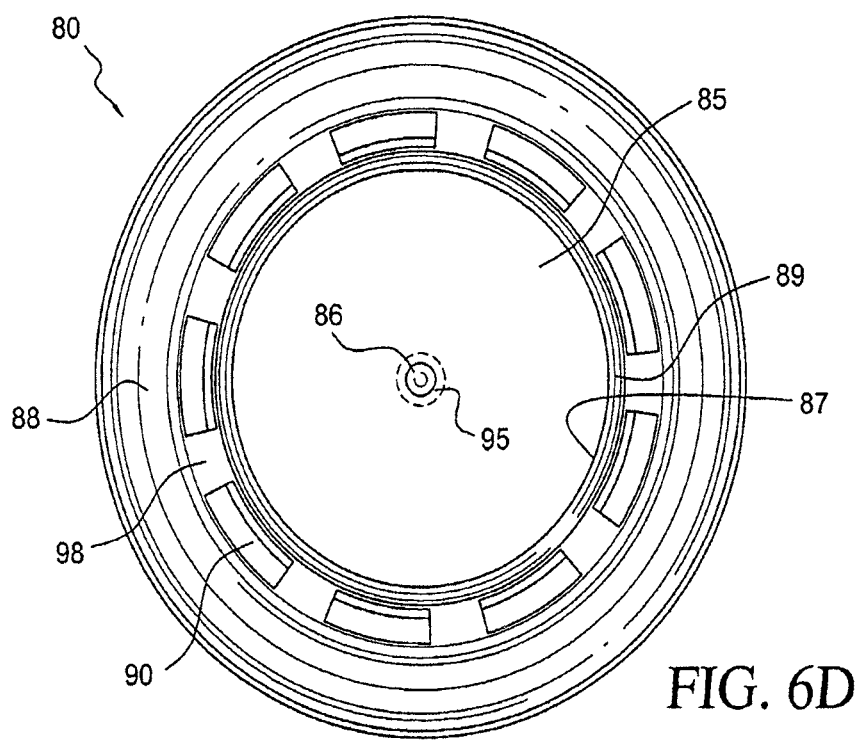

Anterior portion 83 is configured to attach to posterior portion 84 so that anchor 85 is fixedly received within receptacle 95, spacers 90 seat against peripheral step 94, and posterior haptic half 93 sealingly mates with anterior haptic half 88, as depicted in FIG. 6B. When so assembled, haptic halves 88 and 93 form chamber 96 that communicates with space 97 between anterior lens element 85 and substrate 92 through channels 98 disposed between spacers 90. The interior volume of the IOL, including chamber 96 and space 97, is filled with transparent fluid 99, which has an index of refraction selected to match the index of refraction of the surrounding components of IOL 80. Flexible membrane 89 allows edge 87 of anterior lens element 84 to move away from substrate 91 responsive to pressure variations in haptic portion 82.

In accordance with the present invention, haptic halves 88 and 93 of haptic portion 82 comprise a resilient elastic material that permits force applied to those surfaces to the haptic portion to deform. Preferably, when the ciliary muscles contract, the haptic portion is in an unstressed state and assumes a substantially circular cross-section. This corresponds to a maximum internal volume of chamber 96 and a minimum volume of space 97.

When the ciliary muscles relax, the zonules pull the capsule taut, thereby applying compressive forces to the anterior and posterior faces of the haptic portion which in turn cause fluid 99 to pass from chamber 96 through channels 98 and into space 97. Fluid entering space 97 causes edge 87 of anterior lens element 85 to lift in the anterior direction, thereby reducing the convexity of the anterior lens element and reducing the diopter power of the lens. The flexible nature of membrane 89 permits edge 87 to freely deflect when the volume of space 97 increases.

The volume of fluid 99 preferably is selected so that when no external pressure is applied to IOL 80, fluid 99 fills the interior of the IOL and anterior lens element 85 has its most convex shape. Therefore, when pressure is applied to haptic portion 82, fluid 99 migrates beneath anterior lens element 85 to cause IOL 80 to transition to the unaccommodated state.

In addition, the anterior surface of substrate 91 preferably has a predetermined anterior profile, so that in the event of a loss of fluid 99 from the IOL, e.g., resulting in a failure of a seal, the IOL conforms to the anterior profile of the substrate and thus still provides the patient with a desired degree of correction. In a preferred embodiment, substrate 91 is symmetrical, such that peripheral step 94 has a uniform depth. In this case, anterior portion 81 may be attached to substrate 91 at any relative rotational angle.

Anterior lens element 85 may have a constant thickness from the center to the outer edge, or a variable thickness. For example, the anterior lens element may be thinner near anchor 86 with an increasing thickness toward edge 87. Alternatively, the anterior lens element may be thicker near the anchor with a decreasing thickness toward edge 87.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An accommodating intraocular lens comprising:
    an optic comprising a flexible anterior element, a posterior element, an optical axis, the flexible anterior element is the most anterior aspect of the accommodating intraocular lens along the optical axis, the flexible anterior element and the posterior element at least partially defining an optic fluid chamber disposed between the flexible anterior element and the posterior element;
    a haptic portion peripheral to the optic and configured to deform in responsive to ciliary muscle movement, the haptic portion comprising at least one haptic fluid chamber in fluid communication with the optic fluid chamber; and a fluid disposed within the optic fluid chamber and the at least one haptic fluid chamber, wherein the fluid is adapted to be moved between the at least one haptic fluid chamber and the optic fluid chamber in response to deformation of the haptic portion, and wherein a periphery of the flexible anterior element is adapted to be displaced more than a portion of the flexible anterior element disposed along the optical axis in response to movement of the fluid.

2. The intraocular lens of claim 1 wherein the optic portion further comprises an anchor disposed along the optic axis.

3. The intraocular lens of claim 1 wherein the fluid has an index of refraction that is substantially the same as an index of refraction of the anterior element and an index of refraction of the posterior element.

4. The intraocular lens of claim 1 wherein the intraocular lens has an accommodated state in which the flexible anterior element assumes a convex shape and an unaccommodated state in which the periphery of the flexible anterior element is displaced relative to the flexible anterior element along the optical axis to render the flexible anterior element less convex.

5. The intraocular lens of claim 1 wherein the haptic portion comprises a first haptic with a first haptic fluid chamber and a second haptic with a second haptic fluid chamber, the first and second fluid chambers in fluid communication with the optic fluid chamber.

* * * * *